US006599298B1

(12) United States Patent
Forster et al.

(10) Patent No.: US 6,599,298 B1
(45) Date of Patent: Jul. 29, 2003

(54) AUTOMATIC SURGICAL CLIP APPLIER

(75) Inventors: Michel Charles Forster, Le Ruits (FR); Jacques LeBozec, Le Grand Village (FR)

(73) Assignee: Vitalitec International, S.A. (FR)

( * ) Notice: Subject to any disclaimer, the term of this patent is extended or adjusted under 35 U.S.C. 154(b) by 8 days.

(21) Appl. No.: 09/694,524

(22) Filed: Oct. 23, 2000

(51) Int. Cl.[7] ............................................... A61B 17/10
(52) U.S. Cl. ....................................................... 606/139
(58) Field of Search ................................. 606/139, 158, 606/157, 219, 142, 143, 75, 135; 227/19, 21, 901

(56) References Cited

U.S. PATENT DOCUMENTS

| 4,296,751 | A | | 10/1981 | Blake, III et al. | |
|---|---|---|---|---|---|
| 4,425,915 | A | * | 1/1984 | Ivanov | 128/325 |
| 4,850,355 | A | | 7/1989 | Brooks et al. | |
| 5,030,226 | A | | 7/1991 | Green et al. | |
| 5,049,152 | A | | 9/1991 | Simon et al. | |
| 5,100,420 | A | | 3/1992 | Green et al. | |
| 5,197,970 | A | | 3/1993 | Green et al. | |
| 5,330,487 | A | * | 7/1994 | Thornton et al. | 606/143 |
| 5,336,229 | A | * | 8/1994 | Noda | 606/144 |
| 5,383,881 | A | * | 1/1995 | Green et al. | 606/143 |
| 5,395,381 | A | * | 3/1995 | Green et al. | 606/143 |
| 5,423,835 | A | | 6/1995 | Green et al. | |
| 5,514,149 | A | | 5/1996 | Green et al. | |
| 5,527,318 | A | | 6/1996 | McGarry | |
| 5,547,474 | A | | 8/1996 | Kloeckl et al. | |
| 5,607,436 | A | | 3/1997 | Pratt et al. | |
| 5,626,585 | A | | 5/1997 | Mittelstadt et al. | |
| 5,728,110 | A | * | 3/1998 | Vida et al. | 606/143 |
| RE36,720 | E | * | 5/2000 | Green et al. | 606/151 |
| 6,077,290 | A | * | 6/2000 | Marini | 606/205 |
| 6,158,583 | A | * | 12/2000 | Forster | 206/339 |
| 6,273,253 | B1 | * | 8/2001 | Forster et al. | 206/339 |

FOREIGN PATENT DOCUMENTS

| DE | 2546696 | 4/1976 |
|---|---|---|
| DE | 4015562 | 11/1991 |
| EP | 0068046 | 1/1983 |
| EP | 0406724 | 1/1991 |
| EP | 0409569 | 1/1991 |
| EP | 0500353 | 8/1992 |
| EP | 0612505 | 8/1994 |
| EP | 0697198 | 2/1996 |
| EP | 0717962 | 6/1996 |
| EP | 0724862 | 8/1996 |
| EP | 0738500 | 10/1996 |
| WO | WO 82/02825 | 9/1982 |
| WO | WO 89/10094 | 11/1989 |
| WO | WO 90/00376 | 1/1990 |
| WO | WO 90/03763 | 4/1990 |
| WO | WO 96/24294 | 8/1996 |

* cited by examiner

Primary Examiner—John J. Calvert
Assistant Examiner—Alissa L. Hoey
(74) Attorney, Agent, or Firm—Bachman & Lapointe, P.C.

(57) ABSTRACT

An automatic surgical clip applier includes a handle assembly having an actuating member for causing a first member to move sequentially in a distal direction and a proximal direction, and for causing a second member to move sequentially in a proximal direction and a distal direction; and a clip applier assembly adapted for releasably securing to the handle assembly and having a jaw closing member and a clip feeding member, the jaw closing member being engageable with the first member and the clip feeding member being engageable with the second member.

19 Claims, 8 Drawing Sheets

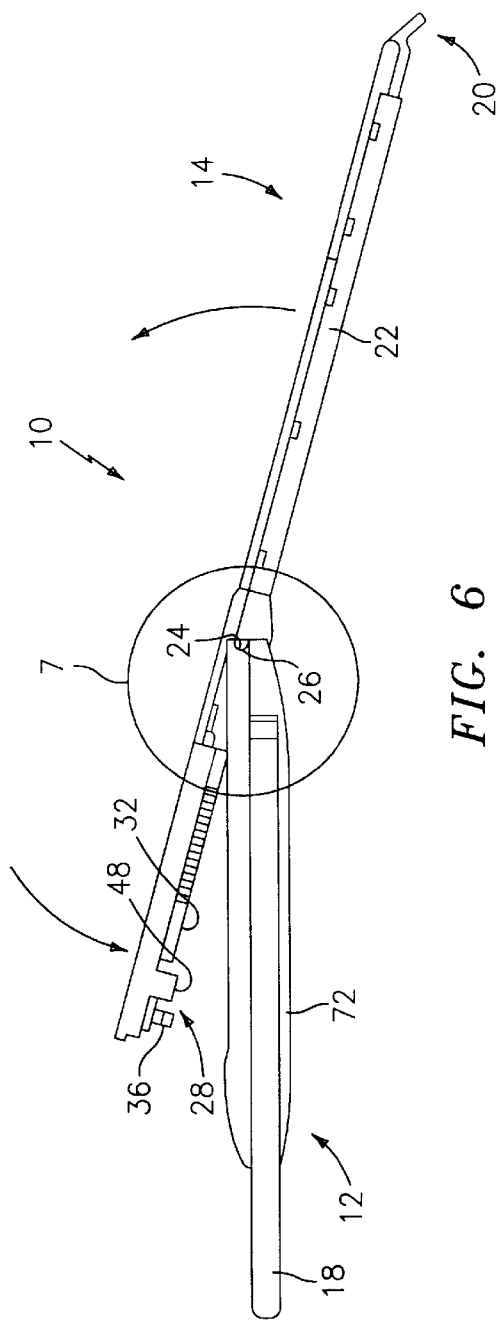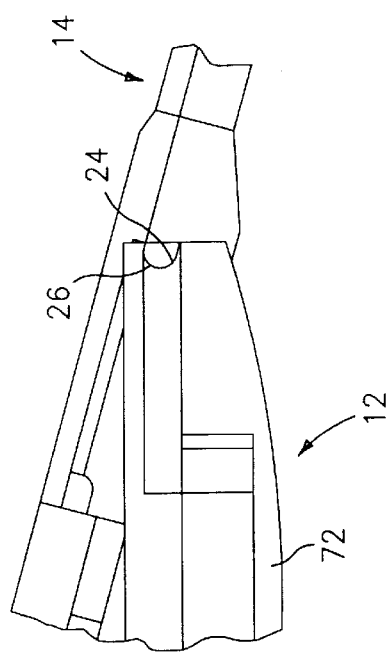
FIG. 6
FIG. 7

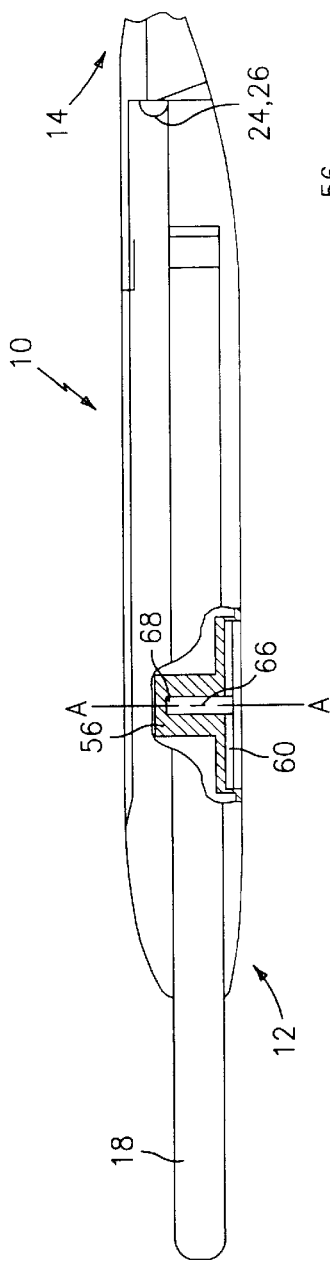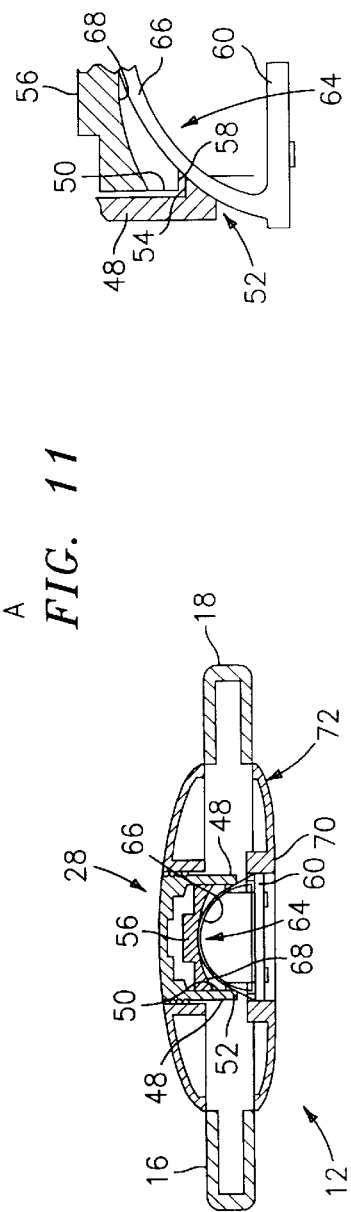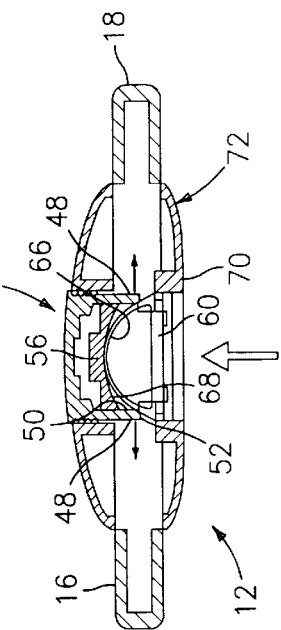

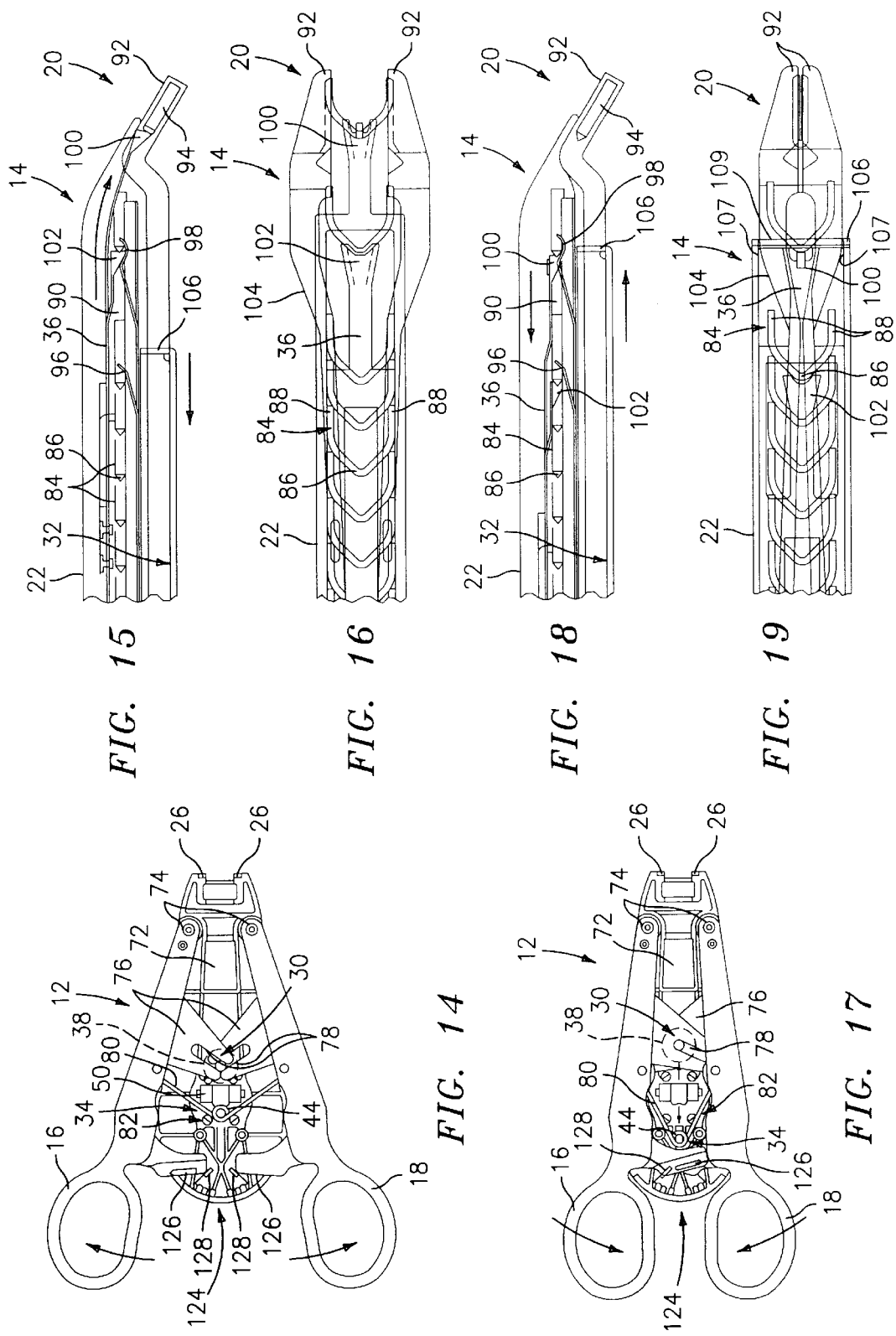

AUTOMATIC SURGICAL CLIP APPLIER

BACKGROUND OF THE INVENTION

The invention relates to an automatic surgical clip applier and, more particularly, to a clip applier having modular assemblies.

Surgical clips are utilized in various surgical procedures in a well known manner so as to ligate tissues, blood vessels and the like.

Surgical devices are known for applying such clips such as hemostatic forceps and the like which can be individually loaded with clips, or which are adapted to contain a supply of clips which are fed, one at a time, to jaws of the device. An example of such a device is as disclosed in U.S. Pat. No. 4,296,751.

Such surgical devices are advantageous in that they allow a surgeon to rapidly apply clips during a procedure without the need for manually loading each clip into the device. However, such devices are typically complex, expensive and in some cases inconvenient or cumbersome for the surgeon to use.

The need remains for a surgical device, specifically an automatic surgical clip applier, which is simple and reliable in use, and which is less expensive to manufacture.

It is a further object of the present invention to provide an automatic surgical clip applier wherein the function is smooth and convenient to the user.

Other objects and advantages of the present invention will appear hereinbelow.

SUMMARY OF THE INVENTION

In accordance with the present invention, the foregoing objects and advantages have been readily attained.

According to the invention, an automatic surgical clip applier is provided which comprises a handle assembly having an actuating member for causing a first member to move sequentially in a distal direction and a proximal direction, and for causing a second member to move sequentially in a proximal direction and a distal direction; and a clip applier assembly adapted for releasably securing to said handle assembly and having a jaw closing member and a clip feeding member, said jaw closing member being engageable with said first member and said clip feeding member being engageable with said second member.

In still further accordance with the present invention, an automatic surgical clip applier is provided which includes a clip applier assembly having jaws for applying said clips and a storage structure for storing a plurality of said clips in a row with said legs extending distally toward said jaws, said storage structure defining a staging position proximally located relative to said jaws, and a waiting position proximally located relative to said staging position; and a clip feeding member slidably mounted relative to said storage structure and having a distal clip engaging member and a proximal clip engaging member, said clip feeding member being slidable from a proximal position to a distal position, wherein sliding of said clip feeding member from said proximal position to said distal position engages said distal clip engaging member with a distally leading clip at said staging position and engages said proximal clip engaging member with a distally second clip at said waiting position, and thereby moves said distally leading clip to said jaws and said distally second clip to said staging position.

The present invention advantageously provides a clip applier having modular assemblies, which allows the handle assembly portion to be reused as much as desired with clip applier cartridges adapted to connect with the assembly. A further advantage of the present invention is that such clip applier cartridges or modules are adapted such that cartridges containing different numbers of clips, and/or cartridges containing clips of different sizes, are all usable with the same handle assembly.

BRIEF DESCRIPTION OF THE DRAWINGS

A detailed description of preferred embodiments of the present invention follows, with reference to the attached drawings, wherein:

FIGS. 6 and 7 illustrate the connection assembly and method for connection of the clip applier assembly of the present invention to the handle assembly of the present invention;

FIGS. 11, 12, 12a and 13 illustrate a latching mechanism release structure in accordance with the present invention;

FIGS. 14, 15 and 16 illustrate the operation of an automatic surgical clip applier in accordance with the present invention during an opening movement of the handle assemblies, FIGS. 17, 18 and 19 illustrate operation of an applier in accordance with the present invention during a closing movement of the handle assembly.

DETAILED DESCRIPTION

The invention relates to an automatic surgical clip applier and, more particularly, to an applier having a handle assembly and a releasably mountable clip applier assembly or cartridge, which allows for the handle assembly to be used with subsequent cartridges after the clip supply in a cartridge is exhausted, and which further allows the same handle assembly to be used with different capacity and/or different clip-size applier cartridges as well.

The present device includes handle portions at one end of the device and jaws for applying clips at the other end of the device. In such devices, it is common to refer to portions relatively toward the jaw end as being "distal" portions, and portions relatively toward the handle end as being "proximal" portions. Thus, such terms when used herein have the meaning as set forth. Specifically, a distal spacing, position or direction is understood to be one generally directed from the handle portions toward the jaws, and a proximal position, spacing or direction is one which is generally directed from the jaws toward the handle portions of the device.

Figure 1:
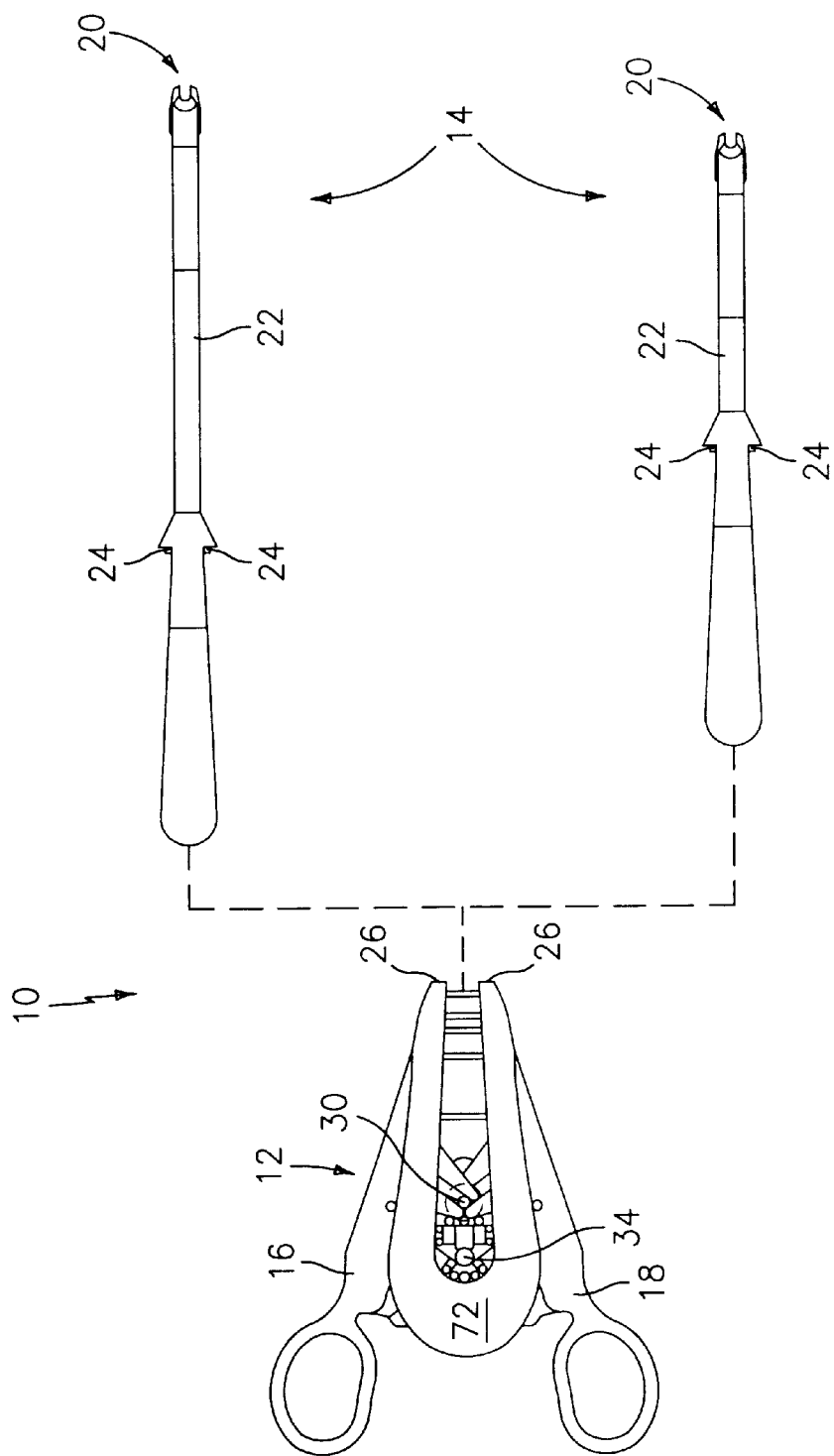
FIG. 1 is a top view of an automatic surgical clip applier in accordance with the present invention.
Figure 2:
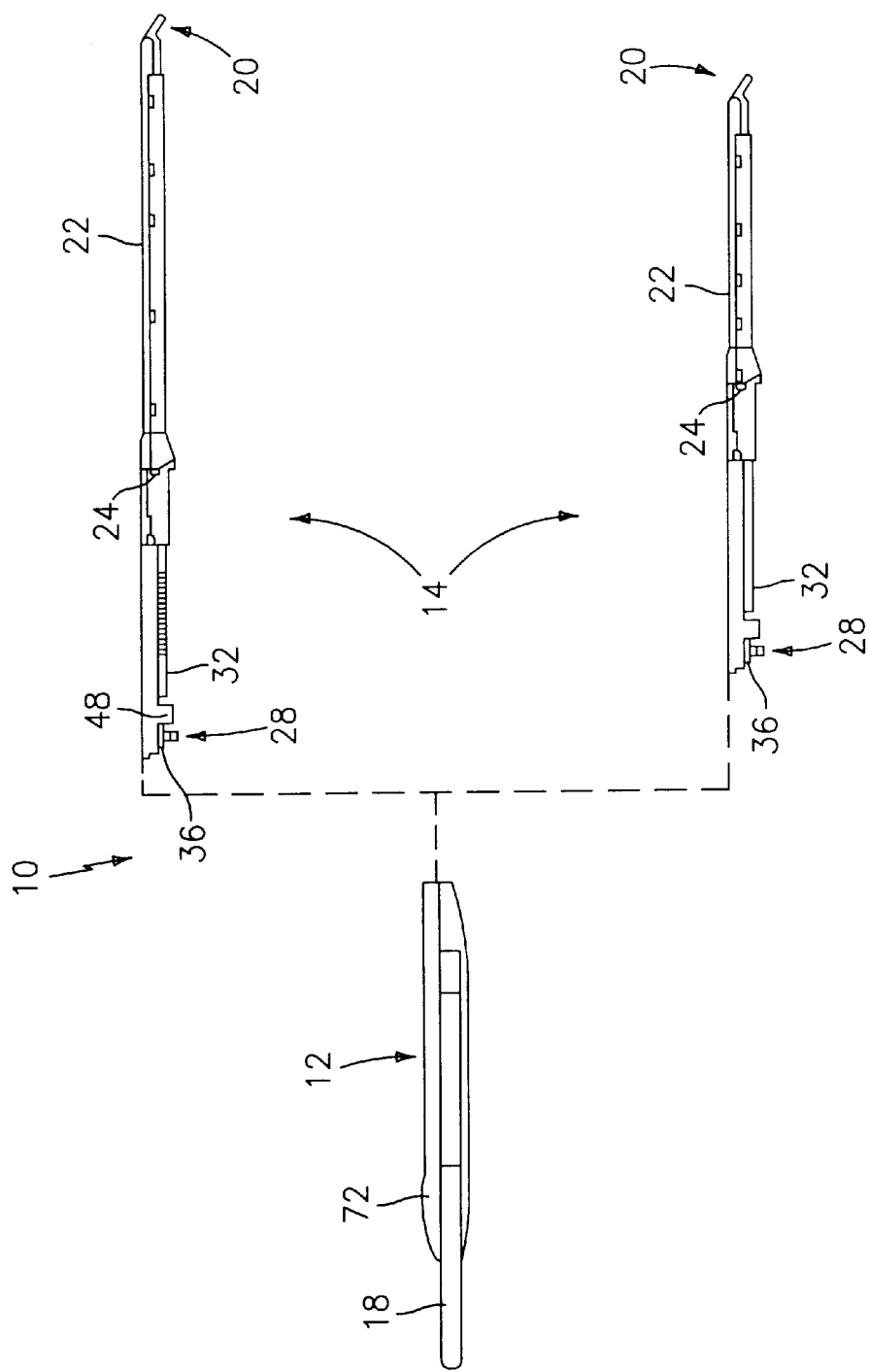
FIG. 2 is a side view of an automatic surgical clip applier in accordance with the present invention.

FIGS. 1 and 2 show an applier 10 in accordance with the present invention including a handle assembly 12 and two different clip applier assemblies 14, each of which can be connected to and used with handle assembly 12 as schematically illustrated.

As will be further discussed in detail below, handle assembly 12 is a portion of applier 10 which is held by a user of applier 10 and actuated or acted upon by the user so as to create motion of different elements within handle assembly 12, and this motion is translated into elements of clip applier assembly 14 for feeding clips to the jaws of the device, and closing a clip in the jaws at a desired location.

Figure 3:
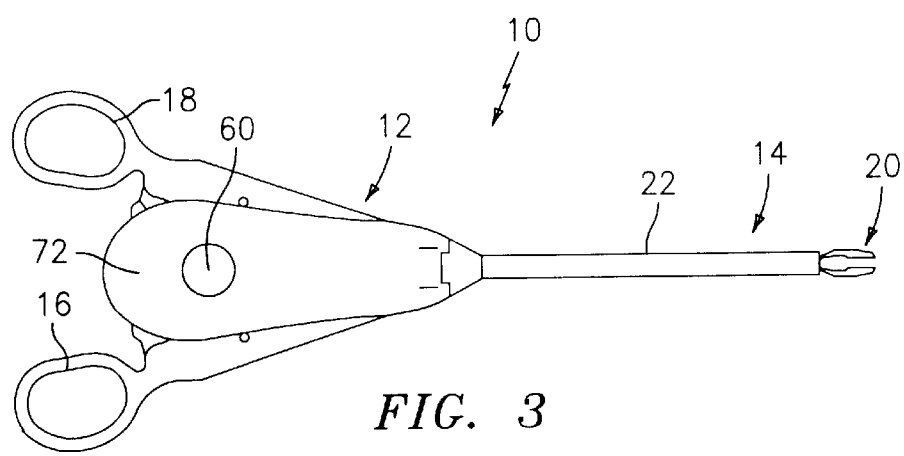
FIGS. 3, 4 and 5 are bottom, side and top views of an assembled automatic surgical clip applier in accordance with the present invention.
Figure 4:
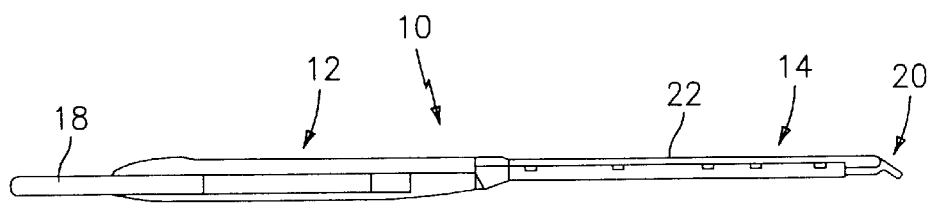
Figure 5:
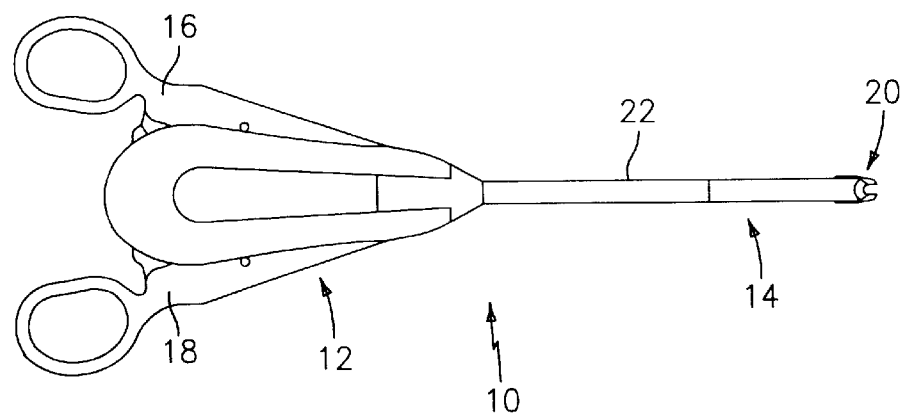

Referring also to FIGS. 3–5, handle assembly 12 advantageously is adapted to be grasped by hand and includes two handle portions 16, 18 which can be manipulated, preferably by opening and closing relative to handle assembly 12, so as to cause the desired clip feeding and applying operation of clip applier assembly 14.

Clip applier assembly 14 as shown typically includes a jaw assembly 20 which is operative to close a clip positioned therein, and jaw assembly 20 is preferably positioned at the distal end of a substantially elongate shaft 22. Handle assembly 12 and clip applier assembly 14 are respectively provided with structure (described in detail below) allowing clip applier assembly 14 to be releasably yet reliably secured to handle assembly 12 for use.

A particularly advantageous aspect of the present invention is the simple, yet reliable mechanism for releasably securing clip applier assembly 14 to handle assembly 12. In accordance with the invention, a pivoting or articulatable structure is preferably provided on handle assembly 12 and clip applier 14 which allows clip applier assembly 14 to be pivotably engaged with handle assembly 12, and a locking structure is further provided on clip applier assembly 14 and handle assembly 12 which can be engaged by pivoting clip applier assembly 14 relative to handle assembly 12 (as shown in FIG. 6) so as to engage the locking mechanism and thereby provide applier 10 in an assembled condition for use.

FIGS. 6 and 7 illustrate one preferred embodiment of a pivotable engaging structure in accordance with the present invention. In this embodiment, clip applier 14 is provided with a substantially outwardly rounded engagement surface 24, and handle assembly 12 is preferably provided with a substantially inwardly rounded engaging surface 26 sized to closely match the shape and contour of engaging surface 24. Engaging surfaces 24, 26 are preferably provided having a straight shape in width, with the curve as shown in FIGS. 6 and 7, whereby engagement of clip applier assembly 14 with handle assembly 12 utilizing surfaces 24, 26 limits all degrees of motion of clip applier 14 relative to handle assembly 12 except for the desired pivot as illustrated by the arrows in FIG. 6, and of course for a separating movement to remove clip applier assembly 14 from handle assembly 12. In order to provide further stability of the device, it is preferable that clip applier assembly 14 bet provided with two engaging surfaces 24 spaced on each side of assembly 14, and that handle assembly 12 be provided with two engaging surfaces 26, also spaced to either side of handle assembly 12 for receiving the spaced engaging surfaces 24.

It should be appreciated that although engaging surfaces 24, 26 are identified as a preferred embodiment of structure for allowing the initial movement of connection of clip applier assembly 14 with handle assembly 12, other structures would certainly be suitable, particularly structures which would serve to securely prevent movement of clip applier assembly 14 relative to handle assembly 12 in a direction transverse to the longitudinal axis of the device.

Figure 8:
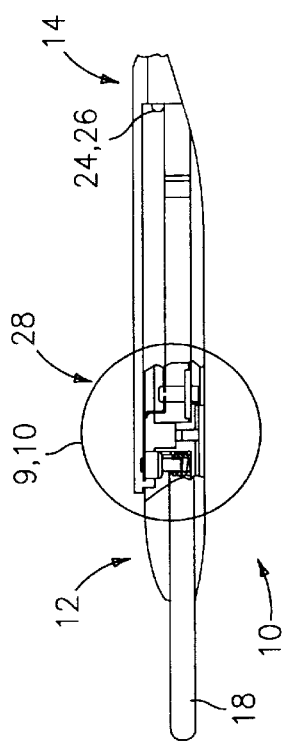
FIGS. 8, 9 and 10 illustrate a latching mechanism of the automatic surgical clip applier of the present invention.
Figure 10:
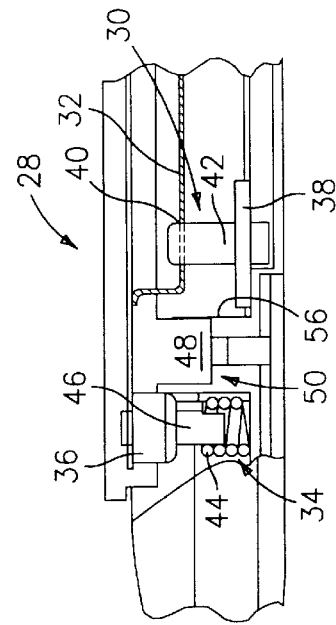
Figure 9:
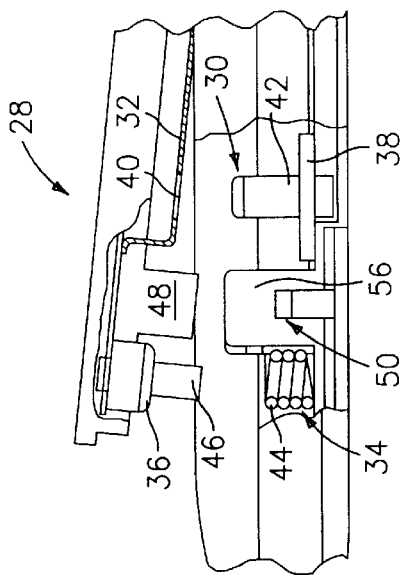

Referring now to FIGS. 8, 9 and 10, a latching mechanism is provided on clip applier assembly 14 and handle assembly 12 in accordance with the present invention for securely holding clip applier assembly 14 relative to handle assembly 12.

Suitable latching structure in accordance with the present invention is preferably any structure which can be simply latched into place, preferably by completion of the pivoting motion as illustrated in FIG. 6, and which remains securely in place until some releasing action for positively releasing the latching is performed, preferably a releasing action which is simple yet difficult to do inadvertently or when not intended.

One suitable latching mechanism 28 is schematically illustrated in FIGS. 8–10, and is further illustrated in FIGS. 12 and 13 to be discussed below.

As set forth above, handle assembly 12 is advantageously used by a surgeon to create the desired function of clip applier assembly 14. In accordance with the present invention, the two functions to be performed are to feed clips to the jaws and to close a clip which is positioned in the jaws. Thus, handle assembly 12 is adapted so as to create the desired motion for carrying out these functions, preferably substantially parallel and oppositely directed motions, and clip applier assembly 14 is adapted to receive such motion and carry out the desired function.

In this regard, handle assembly 12 is preferably provided having a first member 30 for engaging a jaw closing member 32 of clip applier assembly 14, and handle assembly 12 is preferably further provided with a second member 34 for releasably engaging a clip feeding member 36 of clip applier assembly 14.

FIGS. 8–10 show first member 30 as a spool 38 which is acted upon by handle portions 16, 18 as will be further discussed below, and show jaw closing member 32 having an aperture 30 for receiving a post member 42 of spool 38 whereby translation of spool 38 along the axis of applier 10 results in translation of jaw closing member 32 along this axis as desired. As will be further discussed below, jaw closing member 32 when translated along the axis of the device serves to close jaw assembly 20 and thereby close a clip positioned therebetween as desired.

Spool 38 is advantageous in that it has a contour which is functional regardless of alignment relative to handle portions 16, 18 and aperture 30. Of course, other structures could be utilized to transmit motion of handles 16, 18 to jaw closing member 32.

Second member 34 of handle assembly 12 is shown in FIGS. 8–10 as a spring member having a coiled head 44, and clip feeding member 36 is shown having a post member 46 adapted to engage within coiled head 44 such that translation of coiled head 44 along the axis of applier 10 results in translation of post member 46 and clip feeding member 36 of clip applier assembly 14 as desired. As will be further discussed below, translation of clip feeding member 36 along the axis of applier 10 advantageously feeds clips from a storage area to jaw assembly 20 for application as desired.

A particularly advantageous feature of the engagement structures of FIGS. 8–10 is that such structures readily engage when clip applier assembly 14 is pivoted into the latching and connected position relative to handle assembly 12. Further, if these members are not aligned properly during assembly, the misaligned members would prevent connection of clip applier assembly 14 to handle assembly 12, thereby alerting the operator that the elements are not aligned.

Referring now to FIGS. 11–13, latching mechanism 28 is further illustrated, as is the structure of the present invention allowing for release of same.

FIGS. 11–13 show latching mechanism 28 as two substantially parallel and flexible walls 48 each having an inwardly directed ledge 30 which has a beveled side 52 and a substantially flat side 54 (best shown in FIG. 12a). Further, handle assembly 12 is provided with a latch receiving assembly shown as substantially upstanding member 56 having flat surfaces 58 positioned to engage flat side 54 of latching mechanism 28 when clip applier assembly 14 is engaged with handle assembly 12.

It should be readily appreciated that the structure of latching mechanism 28 allows for flat sides 54 and flat surfaces 58 to snap into an engaging position as clip applier assembly 14 is pivoted into the locking position relative to handle assembly 12 as shown in FIG. 6.

Still referring to FIGS. 11–13, a release mechanism is preferably provided, and in this embodiment is provided in the form of a release button 60 having a surface 62 which is accessible to a user of the device, and having structure 64 for disengaging flat sides 54 from flat surfaces 58. In this embodiment, structure 64 is shown as a flexible and curved wall 66 disposed against a non-moving surface 68 of handle assembly 12 such that inward depressing of button 60 as shown by the arrow in FIG. 13 spreads wall 66 laterally, and engagement of wall 66 with ledges 50 spreads ledges 50 laterally and thereby disengages flat sides 54 from flat surfaces 58 so as to allow clip applier assembly 14 to be removed from handle assembly 12, for example to allow an empty clip applier assembly to be discharged and a new one assembled for use.

Button 60 is preferably provided having surface 62 inset or at a lower level as compared to surrounding wall surfaces 70 of handle assembly 12, for example as shown in FIGS. 11–13. This advantageously makes it more difficult to accidentally press button 60 when dis-assembly of applier 10 is not desired.

Turning now to FIGS. 14–19, further details of clip applier assembly 14 and handle assembly 12, as well as operation of same, are provided.

FIGS. 14 and 17 show structure of handle assembly 12 which advantageously provides for the distal and proximal movements of first and second members 30, 34 when handle portions 16, 18 are opened (FIG. 14) and closed (FIG. 17). FIGS. 15, 16, 18 and 19 show structure of clip applier 14 which provides for feeding of clips and closing of clips responsive to the motion of handle assembly 12.

FIG. 14 shows handle assembly 12 including handle portions 16, 18 preferably pivotally connected to a handle body 72, for example at pivot points 74. As shown, each handle portion 16, 18 preferably includes a substantially inwardly directed member 76, each of which defines an inwardly opening slot 78 adapted to receive post member 42 of spool 38. Slots 78 are preferably positioned at an angle relative to handle portions 16, 18 such that closing and opening pivoting of handle portions 16, 18 relative to handle body 72 will cause spool 38 engaged by slots 78 to translate distally and proximally, respectively, as desired.

Handle portions 16, 18 are also preferably provided having structure for engaging arms 80 of the spring 82 having coiled head 44 such that a closing of handle portions 16, 18 relative to each other closes arms 80 of spring 82 and causes proximal movement of coiled head 44 as desired, and opening of handle portions 16, 18 allows opening of arms 80, thereby moving coiled head 44 distally as desired.

Coiled head 44 is advantageous in that a simple structure is utilized to provide for desired motion and also to provide an engageable structure for connection with clip feeding member 316. Of course, other structures could be utilized within the broad scope of the present invention.

FIGS. 15–16 and 18–19 show additional detail of clip applier assembly 14. As shown, clip applier assembly 14 includes a clip cartridge structure preferably defining a storage area for holding clips 84 as desired.

Clips 84 as shown in these figures are preferably clips having an apex portion 86 and legs 88 extending from apex 86, and being made of an acceptable material which is preferably deformable such that a clip can be closed and hold the closed position as desired. Clips 84 are suitably provided of material which is acceptable in the environment of use, and such materials are well known to the person of ordinary skill in the art.

As shown, clip applier assembly 14 preferably includes wall structure defining tracks 90 for slidably holding legs 88 of clips 84, preferably with clips 84 oriented such that legs 88 are positioned to extend distally from apex 86, and with clips 84 in a row as shown such that they can be fed to jaw assembly 20 as desired.

In this regard, jaw assembly 20 preferably includes two laterally spaced jaw members 92 which are axially fixed relative to clip applier assembly 14, and which can be laterally closed and opened as desired. Jaw members 92 preferably further include a slot 94 defined on inner surfaces thereof and positioned as an extension of tracks 90 so as to receive a clip 84 securely therein and prevent escape of clip 84 during closing. In order to further prevent escape, tracks 90 are preferably closed at a distal end thereof so that clips cannot slide distally out of slots 94.

Clips 84 may suitably be biased toward the distal end of clip applier assembly 14 for example by a constant force spring (not shown) or the like, and a leaf spring 96 or other suitable deflectable holding structure is preferably provided so as to hold a lead clip in position until it is desired to move the clip distally. Leaf spring 96 serves to define a waiting position where a clip is held in place until the proper time for deployment distally into a staging position.

In accordance with the present invention, an additional clip retaining member 98 is also preferably provided in a position distally located relative to leaf spring 96, and clip retaining member 98 advantageously serves to define the staging position for holding a clip awaiting deployment into jaw members 92.

Clip feeding member 36 is preferably provided in the form of a slide member slidably mounted relative to clip applier assembly 14 for sliding along the longitudinal axis of clip applier assembly 14 responsive to actuation of handle assembly 12. Clip feeding member 36 preferably extends the length of assembly 14 and is preferably engaged, as discussed above, with second member 34 of handle assembly 12 when clip applier assembly 14 is assembled to handle assembly 12.

Clip feeding member 36 is preferably provided having a distal clip engaging member 100 and proximal clip engaging member 102 which are spaced from each other at a desired distance. Clip engaging member 100 is positioned such that distal movement of clip feeding member 36 from a proximal-most position of same serves to engage a distally leading clip at the staging position, disengage this clip from clip retainer 98, and slide this clip distally from tracks 90 into slots 94 in jaw member 92 whereby this clip is properly positioned for closing as desired.

Proximal clip engaging member 102 is preferably positioned such that distal movement of clip engaging member 36 from the proximal-most position engages clip engaging member 102 with a distally second clip in the waiting position, disengages this clip from leaf spring 96, and slides this clip distally along tracks 90 to the staging position where it is engaged and held by clip retainer 98. Clip engaging members 100, 102 are further preferably provided having proximal surfaces which are sloped as shown in FIGS. 15, 16, 18 and 19 such that proximal movement of clip engaging member 36 from a distal-most position results in substantially free movement of clip engaging members 100, 102 over apex 86 of clips currently positioned at the staging position and waiting position such that clip engaging members 100, 102 can be properly positioned proximally of apexes 86 of these clips for return distal motion as desired.

It is preferred that clip feeding member 36 be provided of a substantially flexible material so that distal clip engaging member 100 can flex downwardly at an angle into tracks 90 of jaw members 92. This is desirable in that it is preferable for jaw members 92 to be angled relative to a longitudinal axis of clip applier assembly 14, preferably at an angle of about 30° relative to same, so that a user of applier 10 can have a better view of jaw members 92 during use in positioning jaw members 92, and a clip held therein, around tissue to be clipped.

FIGS. 15, 16, 18 and 19 further illustrate the distal portions of a jaw closing member 32 which is in this embodiment a slide member engaged with first member 30. Jaw closing member 32 preferably is provided as a slide member slidably mounted to clip applier assembly 14 for translation proximally and distally responsive to movement of handle portions 16, 18. This movement causes closing and opening of jaw members 92 as desired.

The jaw closing function is advantageously provided by forming jaw members 92 at the end of substantially laterally flexible members, each of which is provided with a sloped surface against which jaw closing member 32 is positioned. As shown in FIGS. 16 and 19, sloped surfaces 104 are positioned so that the width of jaw members 92 increases distally along sloped surfaces 104. Jaw closing member 32 is provided as a laterally fixed member 106 which is positioned so as to slidably engage sloped surfaces 104 such that movement of jaw closing member 32 distally from a proximal-most position causes the laterally fixed member 106 to move distally relative to sloped surfaces 104 and thereby inwardly deflect jaw members 92 toward each other. Proximal movement of jaw closing member 32 from the distal-most position moves laterally fixed member 106 proximally relative to sloped surfaces 104 and thereby allows jaw members 92 to return to an open position. Of course, it is preferred that jaw members 92 be mounted at the end of substantially flexible and resilient members such that jaw members 92 will be biased toward the open position. If desired, slots or other structure could be provided to engage member 106 with jaw members 92 such that proximal motion positively opens jaws 92.

In this embodiment, laterally fixed member 106 is shown as two contact surfaces 107 held at a fixed spacing by a connecting member 109 such that contact surfaces 107 contact and interact with sloped surfaces 104 as desired. Of course, other jaw closing structures could be utilized within the broad scope of the present invention.

Still referring to FIGS. 14–19, a full cycle of use of applier 10 in accordance with the present invention will now be discussed. FIGS. 14–16 show applier 10 with handle portions 16, 18 in a fully open position, jaw members 92 in an open position, jaw closing member 32 in a proximal-most position, and clip feeding member 36 in a distal-most position. From this position, handle portions 16, 18 can be pivoted toward the closed position of FIG. 17 as shown by the arrows in FIG. 17 so as to close a clip positioned between the jaws. Such closing motion would cause spool 38 disposed in slots 78 to move distally, thereby moving jaw closing member 32 and laterally fixed member 106 distally relative to jaw members 92 so as to close a clip as shown in FIG. 19.

Such closing motion would further serve to proximally deflect coiled head 44 and clip feeding member 36 engaged therewith so as to move clip engaging members 100, 102 proximally, over clips positioned at the staging position and waiting position respectively, into the proximal-most position of same, where clip feeding member 36 is then ready to feed clips as desired. Opening of handle portions 16, 18 from the position of FIG. 17 to the position of FIG. 14 as shown by the arrow in FIG. 14 will then result in proximal movement of jaw closing member 32 and opening of jaw members 92, as well as distal movement of clip feeding member 36 so as to feed the distally leading clip from the staging position to the jaws, and to feed the distally second clip from the waiting position to the staging position, all as desired. Thus, a closing movement of handle portions 16, 18 serves to close a clip as desired and ready applier 10 for feeding of the next clip, while opening of handle portions 16, 18 serves to open jaw members 92 and feed the next clip for use as desired.

Figure 20:
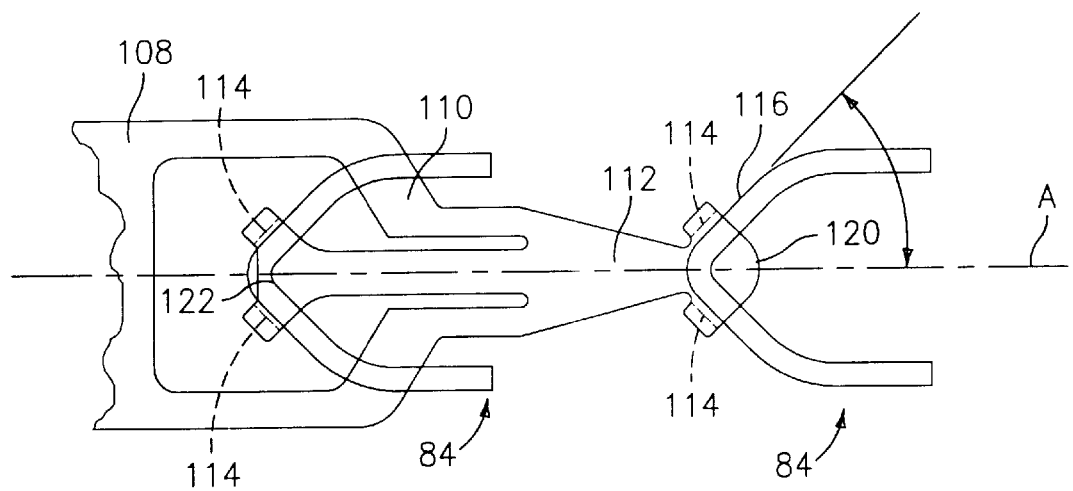
FIGS. 20 and 21 illustrate a preferred embodiment of a clip transfer member in accordance with the present invention.
Figure 21:
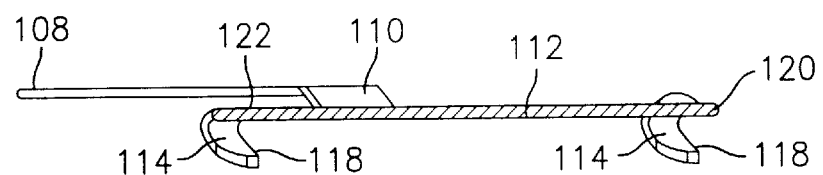

Turning now to FIGS. 20 and 21, Further detail is illustrated in connection with a preferred embodiment of clip feeding member 36.

FIG. 20 shows a distal portion of clip feeding member 36 which is formed from a substantially flat, preferably resilient material that can be formed, stamped or otherwise provided with distal clip engaging member 100 and proximal clip engaging member 102. In this embodiment, clip feeding member 36 may suitably be connected to a slide member 108 by inwardly and downwardly sloped arms 110 which are connected to a support member 112 from which clip engaging members 100, 102 extend. Still further as shown, clip engaging members 100, 102 are preferably provided having clip contacting surfaces 114 which are angled relative to a longitudinal axis A of clip applier 10, preferably at an angle of between about 30 and about 60°, most preferably about 45°. This angle is further preferably selected to align with the side surface 116 of clips 84 to which contact is to be made.

Referring to FIGS. 20 and 21 together, clip contacting surfaces 114 are preferably defined by arms downwardly depending from support member 112. Further, the arms defining clip contacting surfaces 114 preferably further include inwardly extending portions 118 which extend inwardly toward each other. Support member 112 in accordance with this embodiment preferably has a distally extending portion 120 as shown in FIGS. 20 and 21. Contacting surfaces 114 in combination with distally extending portion 120 and inwardly extending portions 118 advantageously serve to define a cradle or notch into which apex 86 and a portion of legs 88 are engaged by clip engaging member 100 so as to provide for stable and secure advancement of the clip as desired. In this embodiment, distally extending portion 120 contacts against an upper side edge of clip 84, while inwardly extending portions 118 contact a lower side edge of clip 84 and clip contacting surfaces 114 contact a proximally directed edge of clip 84.

Proximal clip engaging member 102 is provided in similar fashion and has clip contacting surfaces 114 and inwardly extending portions 118. Further, clip contacting portions 114 and inwardly extending portions 118 of proximal clip engaging member 102 are defined by wall members which extend downwardly from a proximal extension 122 of support member 112, and clips engaged by proximal clip engaging member 102 are engaged by proximal extension 122, clip contacting surfaces 114 and inwardly extending portions 118 thereof in similar fashion to clips engaged by clip engaging member 100.

In further accordance with the present invention, it is particularly advantageous that clip applier assemblies 14 be provided such that the waiting position and staging position of clips be at the same spacing, regardless of the size of clips and/or the number of clips to be held in the clip applier assembly. This spacing may be defined as the spacing between apexes of clips at the respective positions. It is further advantageous for the spacing between apexes of clips at the waiting position and staging position to be the same as spacing between apexes of clips at the staging position and in the jaws. This advantageously allows for handle assembly 12 to be utilized with different clip applier assemblies, specifically with clip applier assemblies containing different size and/or number of clips, since the degrees of motion generated by handle assembly 12 can be selected to match the particular spacing in question, thereby advantageously allowing handle assembly 12 to be utilized with many different types of clip applier assemblies 14.

Returning to FIGS. 14 and 17, it is preferred that handle assembly 12 be provided with a ratchet structure 124 which can advantageously be adapted to prevent opening of handle portion 16, 18 during a closing stroke until handle portions 16, 18 have reached a totally closed position. This advantageously prevents opening of jaw members 92 before a clip is fully closed. As shown in FIGS. 14 and 17, ratchet assembly 124 may suitably be defined by a rack element 126 which may advantageously be defined on handle portions 16, 18, and a ratchet tooth 128 for engaging rack element 126, disposed on handle body 72 and pivotable back to a starting position after handle portions 16, 18 have been fully closed. Of course, other structures could be utilized.

It should be readily apparent that an automatic surgical clip applier has been provided in accordance with the present invention which advantageously allows for the clip cartridge and applier assembly to be provided as a disposable component of the device, thereby allowing the handle assembly to be reused. This advantageously allows for a cost savings to the user of the device. Further, the handle assembly can be prepared as a single generic unit which is useful with different clip applier assemblies, especially with clip applier assemblies having different size and/or numbers of clips, thereby further reducing cost to the user of the device, and allowing for more efficient manufacture as well.

It should further be readily appreciated that the clip transfer assembly of the present invention provides for smooth and reliable feed of clips to the jaws without complicated lost motion or other types of devices, and without complicating the use of applier 10. Further, the preferred clip transfer member securely engages clips in a manner not accomplished by conventional transverse pushing assemblies, thereby further enhancing the stability and reliability of operation of same.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An automatic surgical clip applier, comprising:
   a handle assembly having an actuating member for causing a first member to move sequentially in a distal direction and a proximal direction, and for causing a second member to move sequentially in a proximal direction and a distal direction;
   a clip applier assembly having a jaw closing member and a clip feeding member, said jaw closing member being engageable with said first member and said clip feeding member being engageable with said second member; and
   means for releasably securing said clip applier assembly to said handle assembly, wherein said means for releasably securing comprises a pivot assembly disposed on said handle assembly and said clip applier assembly for pivotably engaging said clip applier assembly with said handle assembly, and a locking assembly for releasably locking said clip applier assembly to said handle assembly.

2. The apparatus according to claim 1, wherein said pivot assembly defines a pivot point in a position spaced distally from said locking assembly.

3. The apparatus according to claim 1, wherein said pivot assembly comprises an outwardly curved surface on one of said clip applier assembly and said handle assembly, and an inwardly curved surface on the other of said clip applier assembly and said handle assembly.

4. The apparatus according to claim 1, wherein said locking assembly comprises an engageable member on one of said clip applier assembly and said handle assembly, an engaging member on the other of said clip applier assembly and said handle assembly and positionable between a locked position for engaging said engageable member and a release position disengaged from said engageable member, and a release member operatively associated with said engaging member for positioning said engaging member to said release position.

5. The apparatus according to claim 4, wherein said engaging member is biased toward said engaging position.

6. An automatic surgical clip applier, comprising:
   a handle assembly having an actuating member for causing a first member to move sequentially in a distal direction and a proximal direction, and for causing a second member to move sequentially in a proximal direction and a distal direction; and
   a clip applier assembly adapted for releasably securing to said handle assembly and having a jaw closing member and a clip feeding member, said jaw closing member being engageable with said first member and said clip feeding member being engageable with said second member, wherein said clip applier assembly further comprises a storage structure for storing a plurality of clips along a longitudinal axis of said clip applier assembly, and a jaw assembly for closing a clip, wherein said clip feeding member is adapted to advance a clip from said storage structure to said jaws.

7. The apparatus according to claim 6, wherein said storage structure defines structure for holding said plurality of clips with a distally leading clip in a staging position and a distally second clip in a waiting position proximally located relative to said staging position, and wherein said clip feeding member comprises a slide member slidably mounted relative to said clip applier assembly and having a distal clip pushing member and a proximal clip pushing member, wherein said slide member is slidable from a proximal position to a distal position, and wherein sliding of said slide member from said proximal position to said distal position engages aid distally leading clip in said staging position with said distal clip engaging member and moves said distally leading clip to said jaw assembly, and engages said distally second clip in said waiting position with said proximal clip engaging member and moves said distally second clip from said waiting position to said staging position.

8. The apparatus according to claim 7, wherein at least one of said distal clip engaging member and said proximal clip engaging member comprises two arms having clip contacting surfaces angled relative to a longitudinal axis of said slide member at an angle between said contacting surface and said axis of between about 30° and about 60°, and wherein said clip contacting surfaces further extend inwardly toward each other so as to define a holding area for holding an clip of a clip with contact surfaces arranged to contact said apex at top, bottom and end surfaces thereof.

9. The apparatus according to claim 7, wherein said clip applier assembly comprises a first assembly containing relatively large clips and a second assembly containing relatively small clips, wherein spacing between an apex of a clip in said staging position and an apex of a clip in said waiting position in said first assembly is the same as said spacing in said second assembly, whereby said first assembly and said second assembly can be used with the same handle assembly.

10. An automatic surgical clip applier, comprising:
a handle assembly having an actuating member for causing a first member to move sequentially in a distal direction and a proximal direction, and for causing a second member to move sequentially in a proximal direction and a distal direction;
a clip applier assembly having a jaw closing member and a clip feeding member, said jaw closing member being engageable with said first member and said clip feeding member being engageable with said second member; and
means for releasably securing said clip applier assembly to said handle assembly, wherein said handle assembly is adapted to provide substantially parallel and oppositely directed movement of said first member and said second member, wherein said handle assembly comprises a handle body and at least one handle member pivotably mounted to said handle body whereby movement of said handle member relative to said handle body in a first direction moves said first member in said distal direction and said second member in said proximal direction, and whereby movement of said handle member relative to said handle body in a second direction moves said first member in said proximal direction and said second member in said distal direction.

11. An automatic surgical clip applier, comprising:
a handle assembly having an actuating member for causing a first member to move sequentially in a distal direction and a proximal direction, and for causing a second member to move sequentially in a proximal direction and a distal direction; and
a clip applier assembly adapted for releasably securing to said handle assembly and having a jaw closing member and a clip feeding member, said jaw closing member being engageable with said first member and said clip feeding member being engageable with said second member, wherein said handle assembly is adapted to provide substantially parallel and oppositely directed movement of said first member and said second member, wherein said handle assembly comprises a handle body and at least one handle member pivotably mounted to said handle body whereby movement of said handle member relative to said handle body in a first direction moves said first member in said distal direction and said second member in said proximal direction, and whereby movement of said handle member relative to said handle body in a second direction moves said first member in said proximal direction and said second member in said distal direction, wherein said handle assembly comprises said handle body and two handle members pivotably mounted to said handle body, wherein each of said two handle members defines an inwardly opening slot member, and wherein said first member comprises a spool disposed in said inwardly opening slot of each of said two handle members whereby pivot of said two handle members toward each other relative to said body member moves said spool in a distal direction.

12. The apparatus according to claim 11, wherein said spool is engageable with said jaw closing member of said clip applier assembly.

13. The apparatus according to claim 11, wherein said second member comprises a spring having a coiled central section and two arms extending from said coiled central portion, and wherein said spring is positioned between said two handle members with said arms extending distally from said coiled central portion and contacting said two handle members, whereby closing of said two handle members pivots said two arms toward each other and moves said coiled central portion in a proximal direction.

14. The apparatus according to claim 13, wherein said coiled central portion is adapted to engage said clip feeding member.

15. An automatic surgical clip applier for applying clips each having an apex portion and legs extending from said apex portion, the applier comprising a clip applier assembly having jaws for applying said clips and a storage structure for storing a plurality of said clips in a row with said legs extending distally toward said jaws, said storage structure defining a staging position proximally located relative to said jaws, and a waiting position proximally located relative to said staging position; and a clip feeding member slidably mounted relative to said storage structure and having a distal clip engaging member and a proximal clip engaging member, said clip feeding member being slidable from a proximal position to a distal position, wherein sliding of said clip feeding member from said proximal position to said distal position engages said distal clip engaging member with a distally leading clip at said staging position and engages said proximal clip engaging member with a distally second clip at said waiting position, and thereby moves said distally leading clip to said jaws and said distally second clip to said staging position.

16. The apparatus according to claim 15, wherein moving said clip feeding member from said distal position to said proximal position engages said distal clip engaging member with a new distally leading clip at said staging position, and engages said proximal clip engaging member with a new distally second clip at said waiting position.

17. The apparatus according to claim 15, wherein spacing between said distal clip engaging member and said proximal clip engaging member is the same as spacing between a clip apex at said staging position and a clip apex at said waiting position.

18. The apparatus according to claim 17, wherein spacing between a clip apex at said jaws and a clip apex at said staging position is the same as spacing between a clip apex at said staging position and a clip apex at said waiting position.

19. The apparatus according to claim 15, wherein at least one of said distal clip engaging member and said proximal clip engaging member comprises two arms having clip contacting surfaces angled relative to a longitudinal axis of said slide member at an angle between said contacting surface and said axis of between about 30° and about 60°, and wherein said clip contacting surfaces further extend inwardly toward each other so as to define a holding area for holding an apex of a clip with contact surfaces arranged to contact said apex at top, bottom and end surfaces thereof.

* * * * *